United States Patent
Goyani et al.

(10) Patent No.: US 11,819,501 B2
(45) Date of Patent: *Nov. 21, 2023

(54) PARENTERAL UNIT DOSAGE FORM OF DIHYDROERGOTAMINE

(71) Applicant: SUN PHARMACEUTICAL INDUSTRIES LIMITED, Maharashtra (IN)

(72) Inventors: Alpesh Goyani, Baroda (IN); Deepak Singodia, Baroda (IN); Bhaskar Pallerla, Baroda (IN); Sudeep Kumar Agrawal, Baroda (IN); Subhas Balaram Bhowmick, Baroda (IN); Rajamannar Thennati, Baroda (IN)

(73) Assignee: SUN PHARMACEUTICAL INDUSTRIES LIMITED

( * ) Notice: Subject to any disclaimer, the term of this patent is extended or adjusted under 35 U.S.C. 154(b) by 0 days.

This patent is subject to a terminal disclaimer.

(21) Appl. No.: 17/712,274

(22) Filed: Apr. 4, 2022

(65) Prior Publication Data

US 2022/0226308 A1 Jul. 21, 2022

Related U.S. Application Data

(63) Continuation of application No. 16/705,435, filed on Dec. 6, 2019, now Pat. No. 11,304,942, which is a continuation of application No. 16/285,495, filed on Feb. 26, 2019, now Pat. No. 10,532,049.

(30) Foreign Application Priority Data

Aug. 27, 2018 (IN) .............. 201821031934

(51) Int. Cl.
A61K 31/48 (2006.01)
A61K 31/4985 (2006.01)
A61K 9/08 (2006.01)
A61K 9/00 (2006.01)
A61P 25/06 (2006.01)
A61M 5/20 (2006.01)

(52) U.S. Cl.
CPC ............ *A61K 31/48* (2013.01); *A61K 9/0019* (2013.01); *A61K 9/08* (2013.01); *A61K 31/4985* (2013.01); *A61M 5/20* (2013.01); *A61P 25/06* (2018.01)

(58) Field of Classification Search
CPC ..... A61M 5/20; A61M 2005/20; A61P 25/06; A61K 31/48; A61K 9/0019; A61K 9/08
See application file for complete search history.

(56) References Cited

U.S. PATENT DOCUMENTS 6,495,535 B1 12/2002 Plachetka et al.
9,943,649 B2 4/2018 Shang et al.
10,456,531 B2 10/2019 Olson et al.
10,532,049 B1 1/2020 Goyani et al.
11,083,712 B1 8/2021 Solarski et al.
11,304,942 B2 * 4/2022 Goyani .................. A61P 25/06
2007/0253913 A1 11/2007 Mohsen et al.
(Continued)

FOREIGN PATENT DOCUMENTS

WO WO-2013169800 A1 * 11/2013 .............. A61M 5/20

OTHER PUBLICATIONS

"D.H.E. 45®" Prescribing Information by Valeant Pharmaceuticals. (Year: 2008).*

(Continued)

*Primary Examiner* — Theodore R. Howell
(74) *Attorney, Agent, or Firm* — Foley & Lardner LLP

(57) ABSTRACT

A parenteral unit dosage form comprising an aqueous solution of dihydroergotamine or pharmaceutically acceptable salt thereof as a sole active ingredient, one or more pH adjusting agents, and optionally one or more co-solvents, wherein the pH of the aqueous solution is such that it contains substantially lower amount of impurity of Formula I and impurity of Formula II as compared to aqueous solution having a pH of 4.0 or less, when the parenteral unit dosage form is stored at 25° C. and 60% relative humidity for at least three months.

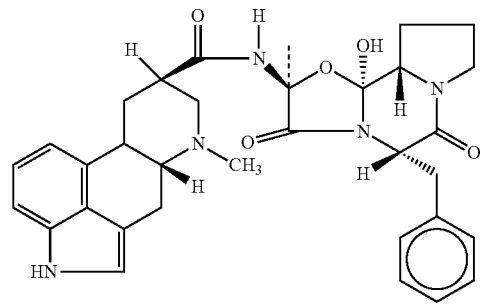

Formula I

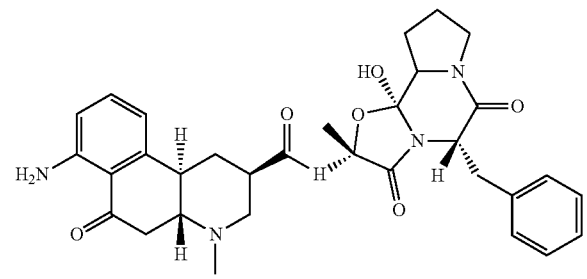

Formula II

9 Claims, No Drawings

(56) References Cited

U.S. PATENT DOCUMENTS

| | | |
|---|---|---|
| 2010/0292653 A1 | 11/2010 | Maritan |
| 2011/0054414 A1 | 3/2011 | Shang et al. |
| 2013/0204199 A1 | 8/2013 | Hourmand et al. |
| 2014/0179705 A1 | 6/2014 | Armer et al. |
| 2014/0262883 A1 | 9/2014 | Devouassoux et al. |
| 2016/0235664 A1 | 8/2016 | Wotton et al. |
| 2020/0108061 A1 | 4/2020 | Goyani et al. |
| 2021/0322392 A1 | 10/2021 | Solarski et al. |

OTHER PUBLICATIONS

U.S. Appl. No. 17/574,816, filed Jan. 13, 2022, Patil et al.
D.H.E 45 Prescribing Information by Valeant Pharmaceuticals North America (Sep. 2009). (Year: 2009).
22 C et al., "Dexamethasone Sodium Phosphate Injection, USP", Nov. 30, 2017, 1 page, Retrieved from the Internet: URL:http://editor.fresenius-kabi.us/Pls/US -PH-Simplist_Dexamethasone_FK-451518_Nov_2 017-Pl.pdf [retrieved on Mar. 24, 2022].
Extended European Search Report, Application No. 19855085.7, dated Apr. 4, 2022, 7 pages.
Hege Helm et al., "Complexation of Dihydroergotamine Mesylate with Cyclodextrin Derivatives: Solubility and Stability in Aqueous Solution", European Journal of Pharmaceutical Sciences, vol. 3, No. 4, Aug. 1, 1995, 7 pages.

\* cited by examiner

PARENTERAL UNIT DOSAGE FORM OF DIHYDROERGOTAMINE

CROSS-REFERENCE TO RELATED APPLICATIONS

This application is a continuation of U.S. patent application Ser. No. 16/705,435, filed Dec. 6, 2019 (now U.S. Pat. No. 11,304,942), which is a continuation of U.S. patent application Ser. No. 16/285,495, filed Feb. 26, 2019 (now U.S. Pat. No. 10,532,049), which claims priority to India Patent Application 201821031934, filed Aug. 27, 2018.

TECHNICAL FIELD

This disclosure relates to migraine and cluster headache treatments. This disclosure specifically relates to a parenteral unit dosage form of dihydroergotamine comprising an aqueous solution of dihydroergotamine or its pharmaceutically acceptable salt.

BACKGROUND

Dihydroergotamine mesylate is the methanesulphonate salt of dehydrogenated ergot alkaloid. It is used for the acute treatment of migraine and cluster headache episodes. Dihydroergotamine is a serotonin receptor agonist and causes vasoconstriction of the intracranial blood vessels. Oral bioavailability of dihydroergotamine is poor and it is not available in oral form in the U.S. Dihydroergotamine is presently marketed both as a nasal spray and as an injectable product in the name of D.H.E. 45® Injection 1 mg/ml, which is supplied in sterile ampoules for intravenous, intramuscular, or subcutaneous administration.

U.S. Pat. No. 6,495,535 B1 discloses an injectable formulation of dihydroergotamine containing 1 mg/ml or 2 mg/ml of dihydroergotamine mesylate, filled in a medicament container (such as a prefilled syringe). The dihydroergotamine formulation includes dihydroergotamine or salts thereof, pharmaceutically acceptable liquid vehicle, organic solvents, antioxidants and pH-adjusting agent, with the pH of the dihydroergotamine mesylate composition at 3.6±0.2. Applicants tested the composition according to U.S. Pat. No. 6,495,535 for chemical stability and it was found that the solution, having a pH of 3.6±0.2, showed unacceptable and high amount of isomeric and oxidative impurities.

There remains a need for a stable solution of dihydroergotamine that provides minimal amount of impurities and is also presented in a self-administrable form.

SUMMARY

This disclosure provides a parenteral unit dosage form comprising an aqueous solution of dihydroergotamine or pharmaceutically acceptable salt thereof as a sole active ingredient, one or more pH adjusting agents, and optionally one or more co-solvents. The pH of the aqueous solution of this disclosure is such that it contains substantially lower amount of impurity of Formula I or impurity of Formula II as compared to aqueous solution having a pH of 4.0 or less, when the parenteral unit dosage form is stored at 25° C. and 60% relative humidity for at least three months.

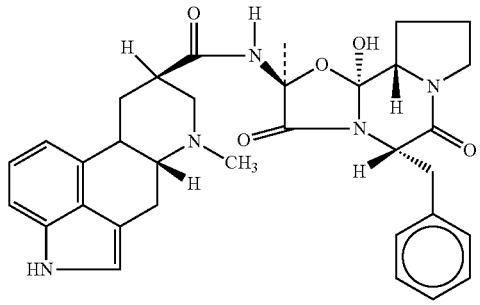

Formula I

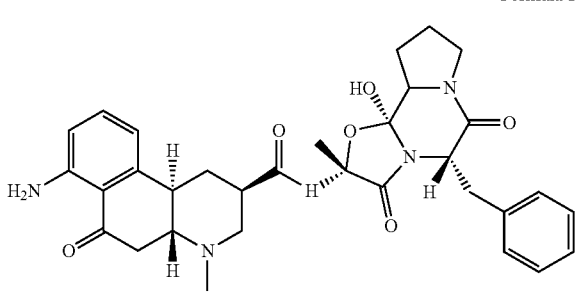

Formula II

This disclosure also provides an auto-injector or a pre-filled syringe comprising the disclosed parenteral unit dosage form. In certain further embodiments, the dosage form is further covered with an overwrap pouch.

This disclosure also provides a method for making the disclosed parenteral unit dosage form comprising an aqueous solution of dihydroergotamine. This unit dosage form has improved chemical stability. The method comprises the step of adjusting the pH of the solution to 4.1 to 4.9 (in certain further embodiments, 4.2 to 4.8 (±0.1)), so that the aqueous solution is such that it contains substantially lower amount of impurity of Formula I or impurity of Formula II as compared to aqueous solution having a pH of 4.0 or less, when the parenteral unit dosage form is stored at 25° C. and 60% relative humidity for at least three months.

Numerous other aspects are provided in accordance with these and other aspects of the invention. Other features and aspects of the present invention will become more fully apparent from the following detailed description and the appended claims.

DETAILED DESCRIPTION

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

As used herein, the phrase 'unit dosage form' refers to dosage form meant for single dose administration. The parenteral dosage form is said to be 'unit dosage form' when the aqueous solution filled in the device such as an autoinjector device can be administered to the patient in single attempt. In certain further embodiments, the aqueous solution is free of a preservative.

As used herein, the percentage of impurities is expressed as percentage by weight of dihydroergotamine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

It has been discovered that the pH of the aqueous solution of dihydroergotamine significantly affects the levels of impurity of Formula I and Formula II. Although impurity of Formula I and Formula II are known structures, the effect of pH on the levels of these impurities on storage was not known or reported. The pH makes a significant impact on control or generation of impurity of Formula I. When the pH of the solution is in the range of 4.1 to 4.9 (in certain further embodiments, 4.2 to 4.8 (±0.1)), substantially lower amount of impurity of Formula I is generated. It was found that substantially higher amount of impurity of Formula I is formed when the pH of the solution is 4.0 or less, such as, for example, pH 3.4 to 3.9. At the pH range of 4.1 to 4.9, the amount of impurity of Formula II generated was substantially lower compared to the amount of impurity of Formula I.

Accordingly, this disclosure provides a parenteral unit dosage form having aqueous solution of dihydroergotamine with improved chemical stability. The parenteral unit dosage form is particularly stable when stored at room temperature, thus allowing the user to store it in an unrestricted manner, instead of storing in specific storage conditions, such as in the refrigerator, or in a cool or dry place.

This disclosure also provides a method for making the disclosed parenteral unit dosage form comprising an aqueous solution of dihydroergotamine. This unit dosage form has improved chemical stability. The method comprises the step of adjusting the pH of the solution to 4.1 to 4.9 (in certain further embodiments, 4.2 to 4.8 (±0.1)), so that the aqueous solution of this disclosure is such that it contains substantially lower amount of impurity of Formula I or impurity of Formula II as compared to aqueous solution having a pH of 4.0 or less, when the parenteral unit dosage form is stored at 25° C. and 60% relative humidity for at least three months.

The disclosed aqueous solution is stable upon storage. The disclosed parenteral unit dosage form is considered to be stable when the aqueous solution of dihydroergotamine contains substantially lower amount of impurity of Formula I or impurity of Formula II as compared to aqueous solution of dihydroergotamine having a pH of 4.0 or less, when the parenteral unit dosage form is stored at 25° C. and 60% relative humidity for at least three months. In certain embodiments, the disclosed parenteral unit dosage form is considered to be stable when the aqueous solution of dihydroergotamine contains substantially lower amount of impurity of Formula I and impurity of Formula II as compared to aqueous solution of dihydroergotamine having a pH of 4.0 or less, when the parenteral unit dosage form is stored at 25° C. and 60% relative humidity for at least three months.

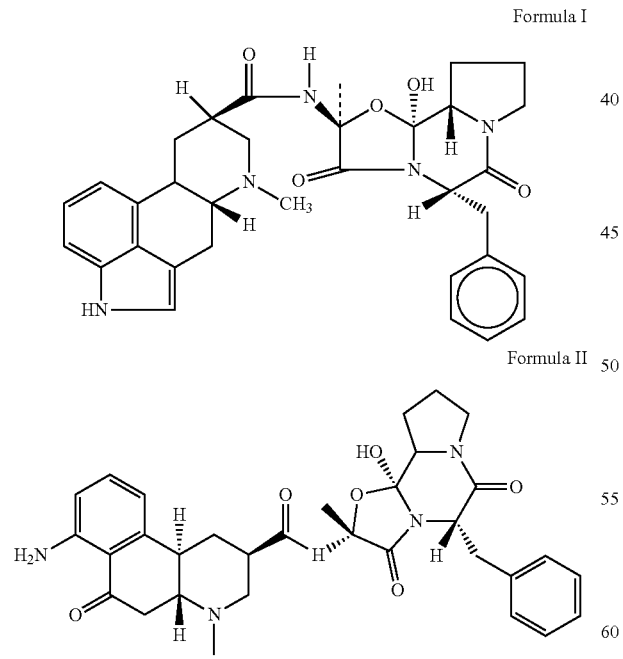

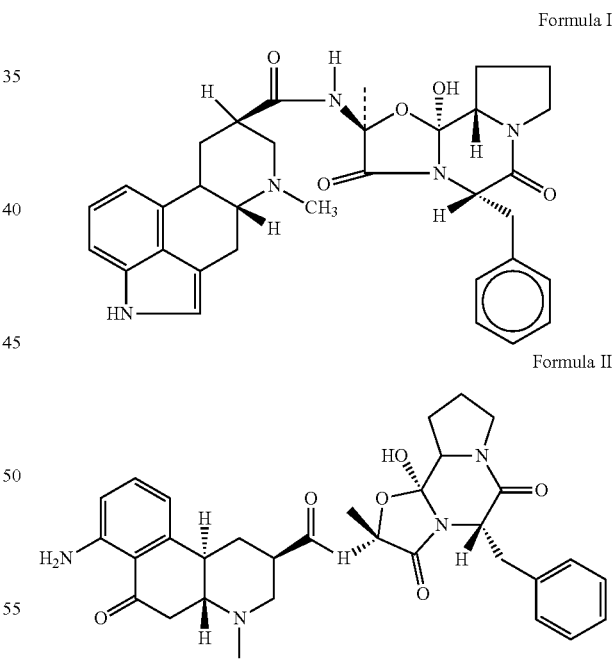

The impurities that are generated in the aqueous solution when stored under accelerated conditions or at room temperature include known as well as unknown impurities. The known impurities are: 2-epi-9, 10-dihydroergotamine, or (6aR,9R,10aR)-N-[(2R,5S,10aS,10bS)-5-benzyl-10b-hydroxy-2-methyl-3,6-dioxooctahydro-8H-oxazolo[3,2-α] pyrrolo[2,1-c]pyrazin-2-yl]-7-methyl-4,6,6a,7,8,9,10,10a-octahydroindolo[4,3-fg]quinoline-9-carboxamide, having chemical structure of Formula I (shown above); and 4R,10R)-7-Amino-4-methyl-6-oxo-1,2,3,4,4a,5,6,10b-octahydro-benzo{quinolone-2-carboxylic acid {(s)-10b-hydroxyl-2-®-methyl-3-6 dioxo-5-[(s)-phenyl methyl)-octahydro-oxazolo[3,2-a] pyrrolo[2,1-c] pyrazine-2-yl]-amide, having chemical structure of Formula II (shown above). The impurities are mainly epimeric, isomeric, and oxidative impurities having the structure as shown in the Formula I and Formula II.

The known and unknown impurities can be separated on a HPLC column Inertsil ODS-3, 150-mm×4.6-mm, 3μ, using mobile phase A containing 3.0 gm of 1-heptane sulphonic acid sodium salt monohydrate in 1000 ml of water, pH adjusted to 2.0±0.05, with orthophosphoric acid and mobile phase B containing the mixture of mobile phase A and acetonitrile in the ratio of 20:80 (% v/v).

As used herein, the term "substantially lower" refers to impurity levels of Formula I or Formula II in the disclosed parenteral unit dosage form at least 20%, or 30%, or 40%, or 50%, or 60% or 70%, or 80%, or 90% lower than the impurity levels present in comparative examples having a pH of aqueous solution of 4.0 or less and also compared to marketed product of dihyroergotamine, which contains solution of dihyroergotamine having a pH of 3.8 and contained in ampoules (D.H.E. 45 Injection in ampoules manufactured by Valeant Pharmaceuticals).

The parenteral unit dosage form is meant for single injection and not for multiple injections and therefore, the solution is not preserved (no preservatives). The parenteral unit dosage form is particularly suitable for single injection and not for multiple injection (i.e., the aqueous solution is free of a preservative). The parenteral unit dosage form is not meant for oral, pulmonary, inhalation, sublingual, nasal, topical or rectal administration.

The disclosed aqueous solution of dihydroergotamine or pharmaceutically acceptable salt thereof is free of an antioxidant, such as, for example, propyl gallate, sodium citrate, butylated hydroxy anisole, sodium metabisulphite, sodium bisulfate, cysteine, 1-methionine.

The disclosed solution is also free of chelating agents, such as, for example, disodium edetate, ethylenediamine tetraacetic acid or its salts. The disclosed solution is also free of complexing agents such as, for example, cyclodextrins or its derivatives.

The aqueous solution is free of wetting agents or surfactants such as, for example, polysorbate, poloxamer, Span, Tweens.

Also, being a parenteral (i.e., an injectable dosage form), the aqueous solution is free of propellants, such as, for example, chlorofluorocarbons, hydroflouroalkanes (such as, for example, dichlorodifluoromethane), nitrogen. The propellants are generally used to deliver the drug in aerosol form.

In certain embodiments, the parenteral unit dosage form does not contain excipients such as mucoadhesive polymers, penetration enhancing agents, surfactants, propellants, and other ingredients that make the aqueous solution suitable for delivery via intranasal or inhalation (pulmonary) route.

The disclosed parenteral unit dosage form is not suitable for sublingual administration as sublingual dosage form.

In certain embodiments, the disclosed aqueous solution of dihydroergotamine mesylate does not contain excipients such as polymers, mucoadhesion promoting agents, wetting agents, surfactants, sugar and sugar alcohols such as mannitol, sorbitol, dextrans, lactose, maltose, saccharose, cyclodextrin, effervescent agents, propellants, and the like, that are suitable for manufacturing of dosage form such as aerosols, dry powder inhalers, nebulizers, vapourizers, metered dose inhalers, drops, spray, patch, tablets, packed powders, paste or gel.

The parenteral unit dosage form comprises an aqueous solution of dihydroergotamine or pharmaceutically acceptable salt thereof as a sole active ingredient in therapeutically effective amount. Examples of suitable pharmaceutically acceptable salts of dihydroergotamine for use in accordance with the present disclosure include, for example, but are not limited to, mesylate, hydrochloride, methanesulfonate, ethanesulfonate, tartrate, maleate, succinate, or other similar salt forms.

In certain embodiments, the dihydroergotamine is the free base. In further embodiments, the pharmaceutically acceptable salt of dihydroergotamine is dihydroergotamine mesylate.

The disclosed parenteral unit dosage form comprises an aqueous solution of dihydroergotamine or pharmaceutically acceptable salt thereof at a concentration of 0.5 mg/ml to 2.0 mg/ml, such as about 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90 or 1.95 mg/ml, in certain embodiments, about 0.75 mg/ml to about 1.5 mg/ml, and in certain further embodiments, in an amount of about 1.0 mg/ml, each unit being filled with the aqueous solution of 1 ml volume. That is, each unit provides about 0.5 mg/ml to about 2.0 mg/ml, such as about 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90 or 1.95 mg/ml, and in certain embodiments, about 0.75 mg/ml to about 1.5 mg/ml per dose comprising an aqueous solution of dihydroergotamine or pharmaceutically acceptable salt thereof as a sole active ingredient, one or more pH adjusting agents and optionally one or more co-solvents, with the pH of the aqueous solution being in the range of 4.1 to 4.9.

In certain embodiments, the pharmaceutically acceptable salt of dihydroergotamine is dihydroergotamine mesylate and it is present at a concentration ranging from 0.5 to 2.0 mg/ml, preferably 0.75 mg/ml to 1.5 mg/ml.

The disclosed aqueous solution has a pH in the range of 4.1 to 4.9, such as, for example, 4.1, 4.15, 4.20, 4.25, 4.30, 4.35, 4.40, 4.45, 4.50, 4.55, 4.60, 4.65, 4.70, 4.75, 4.8, 4.85, 4.9, or intermediate ranges thereof. In further embodiments, the pH is in the range of 4.2 to 4.8 (±0.1). In some other embodiments, the pH of the solution is in the range of 4.1 to 4.8 (±0.1). In some other embodiments, the pH of the solution is in the range of 4.2 to 4.8 (±0.1). In some embodiments, the pH of the solution is in the range of 4.3 to 4.8 (±0.1). In other specific embodiments, the pH of the solution is in the range of 4.35 to 4.8 (±0.1). In some embodiments, the pH of the solution is in the range of 4.4 to 4.8 (±0.1). In another embodiment, the pH of the solution is in the range of 4.45 to 4.8 (±0.1). In further embodiments, the pH of the solution is 4.2 (±0.1).

The pH can be adjusted and maintained in the range of 4.1 to 4.9 by use of one or more pH adjusting agents and/or buffering agents. Examples of suitable pharmaceutically acceptable pH adjusting agent that may be used, include, but are not limited to, citric acid, acetic acid, lactic acid, tartaric acid, fumaric acid, malic acid, hydrochloric acid, sulphuric acid, methane sulphonic acid and/or salts of these acids, tromethamine, potassium hydroxide, sodium hydroxide, or combinations thereof.

The disclosed aqueous solution may comprise physiologically compatible co-solvents such as ethanol, 1,2-propylene glycol, polyglycols, dimethyl sulfoxide, glycerol, triglycerides, partial esters of glycerine or mixtures thereof. In some embodiments, the co-solvent is a mixture of ethanol and glycerine or glycerol.

The disclosed parenteral unit dosage form is suitable for administering the aqueous solution of dihydroergotamine by subcutaneous route or intra-muscular route. The aqueous solution is suitable for direct subcutaneous administration, i.e. it is ready-to-inject or ready-to-self-administer. Reconstitution or dilution before use is not needed.

The disclosed parenteral unit dosage form comprising an aqueous solution of dihydroergotamine mesylate is suitable for acute treatment of migraine headaches with or without aura or for acute treatment of cluster headache episodes.

The volume of aqueous solution of dihydroergotamine filled in the parenteral unit dosage form ranges from about 0.5 ml to 10.0 ml; in further embodiments, 1.0 ml to 2.0 ml, and in yet further embodiments, 1.0 ml. According to certain embodiments, the aqueous solution of dihydroergotamine is filled in the parenteral unit dosage form in volume of 1.0 ml.

In some embodiments, the parenteral unit dosage form is in the form of an autoinjector or a prefilled syringe. In certain embodiments, the dosage form is an autoinjector. The autoinjector or prefilled syringe acts as a primary container of the aqueous solution of dihydroergotamine. In some embodiments, the parenteral unit dosage form is in the form of a prefilled syringe. The prefilled syringe comprises a reservoir, such as, for example, a barrel or a cartridge to store the aqueous solution; a stalked needle attached at one end of the reservoir; a needle shield or tip cap that covers the needle and seals the needle tip opening; optionally a rigid shield covering the needle shield or tip cap; a plunger stopper at the other end of the reservoir that stoppers and seals the aqueous solution filled in the reservoir; and a plunger rod that fits into the plunger stopper and is used to push the plunger stopper along with the solution towards the needle end while administering the aqueous solution of dihydroergotamine. The reservoir of the prefilled syringe may be made up of glass, plastic or polymeric material. The plastic or polymeric material may be selected from, but not limited to, cycloolefin polymer, cycloolefin copolymer, polyolefin, styrene-polyolefin based polymers and block co-polymers, polycarbonates. The plunger stopper, the stopper valve or the tip cap of the injection device may be made of a rubber or elastomeric material, or other suitable material such as high density polyethylene or low density polyethylene. In some embodiments, the plunger stopper or tip cap is made of rubber or elastomeric material selected from bromobutyl rubber, chlorobutyl rubber, styrene butadiene rubber. The parenteral unit dosage form can deliver to a patient via a needle to a depth under the skin of 5.5 mm±1.5 mm. When the injection is a subcutaneous injection, the injection volume ranges from 0.5 ml to 1 ml, administered using an auto-injector when the unit dose of dihydroergotamine mesylate is from 0.5 mg to 1 mg.

In some embodiments, the aqueous solution is filled in the glass barrel stoppered with the black chlorobutyl rubber stopper at one end, and the solution remains in direct contact with the rubber stopper during the shelf life of the parenteral unit dosage form. It was found that there was no unacceptably high levels of impurity of Formula I or Formula II during storage, even though the aqueous solution remains in direct contact with the rubber stopper during its shelf life.

In some embodiments, the parenteral unit dosage form is packaged or enclosed in a secondary packaging. The secondary packaging may comprise a pouch or a blister pack and/or an opaque carton. In further embodiments, the secondary packaging is an overwrap pouch. The parenteral unit dosage form may be packed in a pouch from which oxygen has been excluded, such that the pouch that contains less than 1% of oxygen. Further, a suitable oxygen scavenger may be placed inside the pouch. In some embodiments, the pouch or any other secondary packaging comprises a triple laminated aluminum pouch and an oxygen scavenger. In further embodiments, the parenteral unit dosage form is placed in a secondary packaging comprising triple laminated aluminum pouch and an oxygen scavenger (Ageless® oxygen scavenger with capacity of 500 ml). In certain embodiments, an oxygen scavenger is placed between the primary container, i.e., for example, a syringe and the secondary packaging, for example, an aluminium pouch. The stability of the aqueous solution is found to be improved when the parenteral unit dosage form comprises a secondary overwrap pouch along with an oxygen scavenger.

Particularly, it was found that impurity of Formula II was substantially controlled when oxygen scavenger was placed in the secondary packaging (such as the pouch), irrespective of the pH of the solution, compared to absence of oxygen scavenger. However, the impurity of Formula I was particularly controlled and was found to be minimum only when the pH of the solution was 4.1 to 4.9, with or without the presence of oxygen scavenger in the secondary pouch. At lower pH of 3.4 to 3.9, the impurity of Formula I was comparatively higher.

In certain embodiments, the parenteral unit dosage form comprises an aqueous solution of dihydroergotamine or pharmaceutically acceptable salt thereof as a sole active ingredient, one or more pH adjusting agents, and optionally one or more co-solvents, wherein the pH of the aqueous solution ranges from 4.1 to 4.9 (in some embodiments, between 4.2 to 4.8 (±0.1)). The parenteral unit dosage form is placed in an overwrap pouch, optionally with an oxygen scavenger. The parenteral unit dosage form is found to be stable on storage in that the aqueous solution contains substantially lower amount of an impurity of Formula I or impurity of Formula II or total impurities, as compared to aqueous solution having pH 4.0 or lower, at any time point during shelf life storage.

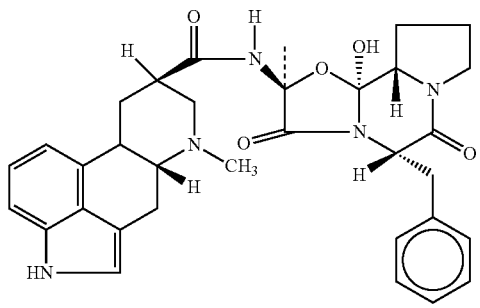

Formula I

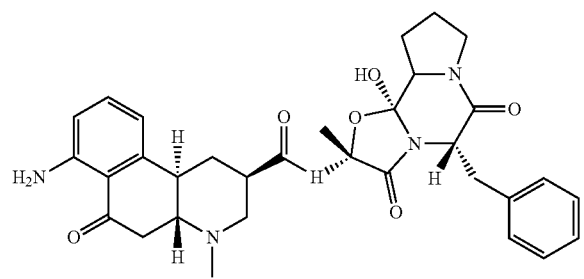

Formula II

In some embodiments, the pharmaceutically acceptable salt of dihydroergotamine is dihydroergotamine mesylate and it is present at a concentration ranging from 0.5 to 2.0 mg/ml, preferably 0.75 to 1.5 mg/ml. The aqueous solution is present in an auto-injector or prefilled syringe overwrapped by a pouch and optionally having an oxygen scavenger. The aqueous solution is free of antioxidant, preservatives, chelating and complexing agents. The parenteral unit dosage form is suitable for single parenteral administration and not for multiple doses. The parenteral unit dosage form is not suitable for oral, sublingual, nasal, pulmonary, topical or rectal administration.

In some embodiments, the substantially lower amount of impurities is such that impurity of Formula I is less than 0.25% by weight, the impurity of Formula II is less than 1.4% by weight and an increase in the total amount of impurities as compared to an initial amount of impurities is less than 2.6% by weight, when the parenteral unit dosage form having a pH of 4.1 to 4.9 is placed in a pouch and stored at 25° C. and 60% relative humidity for three months as compared to a parenteral unit dosage form having a pH of 4.0 or less, such as 3.4 to 3.9. In this aspect, the substantially lower amount of impurities is such that impurity of Formula I is less than 0.7% by weight and less than 1.7% by weight increase in the total amount of impurities as compared to an initial amount of impurities, when the parenteral unit dosage form is placed in a pouch and stored at 40° C. and 75% relative humidity for one month.

The disclosed parenteral unit dosage form in a prefilled syringe comprising an aqueous solution of dihydroergotamine or its pharmaceutically acceptable salt, with pH in the range of 4.1 to 4.9, shows better chemical stability in comparison to marketed product of dihyroergotamine, which contains solution of dihyroergotamine having a pH of 3.8 and contained in ampoules (D.H.E. 45® Injection in ampoules manufactured by Valeant Pharmaceuticals).

In some embodiments, the disclosed parenteral unit dosage form of dihydroergotamine comprises or consists essentially of, or consists of the following composition. See Table 1.

TABLE 1

|  | Concentration Range (mg/ml) |
| --- | --- |
| A. Aqueous solution having - | |
| Dihydroergotamine or its pharmaceutically acceptable salt | 0.5 to 2.0 |
| Co-solvent | q.s. to solubilize dihydroergotamine or its salt |
| pH adjusting agent | q.s. to pH 4.1 to 4.9 |
| Aqueous Vehicle | q.s. to 1 ml |
| B. Container selected from Autoinjector device or pre-filled syringe containing the above aqueous solution of Dihydroergotamine | |
| C. An overwrap pouch covering the container. | | q.s.—quantity sufficient

In some embodiments, the disclosed parenteral unit dosage form of dihydroergotamine comprises or consists essentially of, or consists of the following composition. See Table 2.

TABLE 2

|  | Concentration Range (mg/ml) |
| --- | --- |
| A. Aqueous solution having - | |
| Dihydroergotamine or its pharmaceutically acceptable salt | 0.5 to 2.0 |
| Co-solvent | q.s. to solubilize dihydroergotamine or its salt |
| pH adjusting agent | q.s. to pH 4.1 to 4.9 |
| Aqueous Vehicle | q.s. to 1 ml |
| B. Container selected from Autoinjector device or pre-filled syringe containing the above aqueous solution of Dihydroergotamine | |
| C. An overwrap pouch covering the container and having an oxygen scavenger. | | q.s.—quantity sufficient

In some embodiments, the disclosed parenteral unit dosage form of dihydroergotamine comprises or consists essentially of, or consists of the following composition. See Table 3.

TABLE 3

|  | Concentration Range (mg/ml) |
| --- | --- |
| A. Aqueous solution having - | |
| Dihydroergotamine or its pharmaceutically acceptable salt | 0.5 to 2.0 |
| Alcoholic Co-solvent | q.s. to solubilize dihydroergotamine or its salt |

TABLE 3-continued

|  | Concentration Range (mg/ml) |
|---|---|
| pH adjusting agent | q.s. to pH 4.2 to 4.8 (±0.1) |
| Aqueous Vehicle | q.s to 1 ml |
| B. Container selected from Autoinjector device or pre-filled syringe containing the above aqueous solution of Dihydroergotamine | |
| C. An overwrap pouch covering the container. | | q.s.—quantity sufficient

In some embodiments, the disclosed parenteral unit dosage form of dihydroergotamine comprises or consists essentially of, or consists of the following composition. See Table 4.

TABLE 4

|  | Concentration Range (mg/ml) |
|---|---|
| A. Aqueous solution having - | |
| Dihydroergotamine or its pharmaceutically acceptable salt | 0.5 to 2.0 |
| Alcoholic Co-solvent | q.s. to solubilize dihydroergotamine or its salt |
| pH adjusting agent | q.s. to pH 4.2 to 4.8 (±0.1) |
| Aqueous Vehicle | q.s to 1 ml |
| B. Container selected from Autoinjector device or pre-filled syringe containing the above aqueous solution of Dihydroergotamine | |
| C. An overwrap pouch covering the container and having an oxygen scavenger. | | q.s.—quantity sufficient

In some embodiments, the disclosed parenteral unit dosage form of dihydroergotamine comprises or consists essentially of, or consists of the following composition. See Table 5.

TABLE 5

|  | Concentration Range (mg/ml) |
|---|---|
| A. Aqueous solution having- | |
| Dihydroergotamine or its pharmaceutically acceptable salt | 0.75 to 1.5 |
| Ethanol | 100-200 |
| Glycerine | 40-60 |
| Methane sulfonic acid and sodium hydroxide | q.s. to pH 4.1 to 4.9 |
| Water for Injection | q.s to 1 ml |
| B. Container selected from Autoinjector device or pre-filled syringe containing the above aqueous solution of Dihydroergotamine | |
| C. An overwrap pouch covering the container and having an oxygen scavenger. | | q.s.—quantity sufficient

In some embodiments, the disclosed parenteral unit dosage form of dihydroergotamine comprises or consists essentially of, or consists of the following composition. See Table 6.

TABLE 6

|  | Concentration Range (mg/ml) |
|---|---|
| A. Aqueous solution having- | |
| Dihydroergotamine or its pharmaceutically acceptable salt | 0.75 to 1.5 |
| Ethanol | 100-200 |
| Glycerine | 40-60 |
| Methane sulfonic acid and sodium hydroxide | q.s. to pH 4.1 to 4.9 |
| Water for Injection | q.s to 1 ml |
| B. Container selected from Autoinjector device or pre-filled syringe containing the above aqueous solution of Dihydroergotamine | |
| C. An overwrap pouch covering the container and having an oxygen scavenger. | | q.s.—quantity sufficient

In some embodiments, the disclosed parenteral unit dosage form of dihydroergotamine comprises or consists essentially of, or consists of the following composition. See Table 7.

TABLE 7

| | Concentration Range (mg/ml) |
|---|---|
| A. Aqueous solution having- | |
| Dihydroergotamine mesylate | 1.0 |
| Ethanol | 140-160 |
| Glycerine | 45-55 |
| Methane sulfonic acid and sodium hydroxide | q.s. to pH 4.2 to 4.8(±0.1) |
| Water for Injection | q.s to 1 ml |
| B. Container selected from Autoinjector device or pre-filled syringe containing the above aqueous solution of Dihydroergotamine | |
| C. An overwrap pouch covering the container. | | q.s.—quantity sufficient

In some embodiments, the disclosed parenteral unit dosage form of dihydroergotamine comprises or consists essentially of, or consists of the following composition. See Table 8.

TABLE 8

| | Concentration Range (mg/ml) |
|---|---|
| A. Aqueous solution having- | |
| Dihydroergotamine mesylate | 1.0 |
| Ethanol | 140-160 |
| Glycerine | 45-55 |
| Methane sulfonic acid and sodium hydroxide | q.s. to pH 4.2 to 4.8(±0.1) |
| Water for Injection | q.s to 1 ml |
| B. Container selected from Autoinjector device or pre-filled syringe containing the above aqueous solution of Dihydroergotamine | |
| C. An overwrap pouch covering the container and having an oxygen scavenger. | | q.s.—quantity sufficient

EXAMPLES

For this invention to be better understood, the following examples are set forth. These examples are for purposes of illustration only and are not be construed as limiting the scope of the invention in any manner.

Example 1

TABLE 9

| Aqueous solution of dihydroergotamine mesylate | |
|---|---|
| Ingredient | Amount in mg/mL |
| Dihydroergotamine Mesylate | 1.0 |
| ethanol | 49.32 (0.061 ml/ml) |
| Glycerine | 150 |
| Methanesulphonic acid | q.s. to adjust pH to 4.4 ± 0.2 |
| Sodium Hydroxide | q.s. to adjust pH to 4.4 ± 0.2 |
| Water for Injection | q.s to 1 mL |

Step 1: Water for Injection was collected in a closed jacketed manufacturing tank and cooled to 2-8° C. with chilled water circulation with simultaneous sparging with nitrogen or argon to get dissolved oxygen content less than 1 ppm. Dispensed quantity of glycerine was added to the water for Injection under stirring and pH of solution was adjusted to 4.4±0.2 using 0.5% w/v methanesulphonic acid solution. Alcohol was added to above solution under stirring at 2-8° C. and the dissolved oxygen content was maintained below 1 ppm using nitrogen purging.

Step 2: The dispensed quantity of dihydroergotamine mesylate was added to the solution of step 1 under stirring and was stirred until complete dissolution of dihydroergotamine mesylate. The pH of solution was checked and if required the pH was adjusted to 4.4±0.2 using 0.5% w/v sodium hydroxide solution and 0.5% w/v methanesulphonic acid solution.

Step 3: The volume was made up with water for Injection. The final solution was filtered under nitrogen pressure through 0.2 μm PVDF pre-filter followed by 0.2 μm PVDF sterilizing grade filter under diffused light/sodium vapour lamp and filled in 1 mL syringe at standard fill volume 1.05 ml±2% (0.02 ml) with pre and post-nitrogen flushing. The stoppering of PFS was done under vacuum to avoid any air bubble.

Step 4: The filled and stoppered prefilled syringe was assembled into an autoinjector device Example 2

The auto-injector device filled with the aqueous composition of dihydroergotamine of Example 1 was placed in aluminum pouch with the oxygen scavenger and sealed. The solution was subjected to stability under condition of 25° C./60% relative humidity and at 40° C./75% relative humidity. The impurity levels were determined by separating the known and unknown impurities on a HPLC column using suitable mobile phase and quantified. Dihydroergotamine solutions as per Example 1, but with varying pH to 3.9, 4.0 and 4.2, were prepared. These were subjected to chemical stability study under the accelerated storage conditions namely, 25° C./60% relative humidity for six months and 40° C./75% relative humidity for three months. The results are tabulated below in Table 10.

TABLE 10

Effect of pH on the known and unknown impurity levels at different storage conditions

| | | When stored at 25° C./60% relative humidity for six months | | |
|---|---|---|---|---|
| Aqueous solution of Table 9 adjusted to pH = X pH | | Levels of impurity of Formula I in % | Levels of impurity of Formula II in % | Increase in total impurities from initial |
| Comparative Example 1 | pH 3.9 | 0.67 | 1.97 | 4.14 |
| | pH 4.0 | 0.84 | 0.17 | 1.01 |
| Example 2 (an embodiment of the disclosed dosage form) | pH 4.2 | 0.45 | 0.14 | 0.61 |

| | | When stored at 40° C. and 75% relative humidity for three months | | |
|---|---|---|---|---|
| Aqueous solution of Table 9 adjusted to pH = X pH | | Levels of impurity of Formula I in % | Levels of impurity of Formula II in % | increase in total impurities from initial |
| Comparative Example 1 | pH 3.9 | 4.26 | 0.41 | 5.07 |
| | pH 4.0 | 2.77 | 0.12 | 3.03 |
| Example 2 (an embodiment of the disclosed dosage form) | pH 4.2 | 1.55 | 0.11 | 1.78 |

It was observed that the parenteral unit dosage form comprising aqueous solution of dihydroergotamine or its pharmaceutically acceptable salt having a pH of 4.2 (Example 2) when placed in an overwrap pouch with an oxygen scavenger and stored at 25° C. and 60% relative humidity or at 40° C. and 75% relative humidity, showed substantially lower amount of impurity of Formula I and lower amount of total impurities compared to a parenteral unit dosage forms that comprise aqueous solution of dihydroergotamine having a lower pH of 3.9 to 4.0.

Example 3

The dihydroergotamine solutions as per Example 1 were prepared by varying pH to 3.4, 3.7, 3.8, 3.9, 4.1, 4.5 and 4.8. The auto-injector device filled with these aqueous solutions of dihydroergotamine were placed in aluminum pouch and sealed and were subjected to stability testing under condition of 25° C./60% relative humidity and at 40° C./75% relative humidity. The impurity levels were determined by separating the known and unknown impurities on a HPLC column using suitable mobile phase and quantified. The results are tabulated below in Table 11.

TABLE 11

Effect of pH on the known and unknown impurity levels at different storage conditions

| | | Levels of impurity of Formula I in % | Levels of impurity of Formula II in % | Increase in total impurities from initial |
|---|---|---|---|---|
| Aqueous solution of Table 9 adjusted to pH = X pH | | When stored at 25° C./60% relative humidity for 3 Months | | |
| Comparative Example 2 | pH 3.4 | 0.76 | 1.42 | 3.11 |
| | pH 3.7 | 0.38 | 1.44 | 2.86 |
| | pH 3.8 | 0.48 | 1.90 | 3.76 |
| | pH 3.9 | 0.28 | 1.74 | 3.16 |
| Example 3 (an embodiment of the disclosed dosage form) | pH 4.1 | 0.22 | 1.33 | 2.48 |
| | pH 4.5 | 0.12 | 0.97 | 1.59 |
| | pH 4.8 | 0.10 | 0.75 | 1.17 |

| | | When stored at 40 C. and 75% relative humidity for one month | | |
|---|---|---|---|---|
| Aqueous solution of Table 9 adjusted to pH = X pH | | Levels of impurity of Formula I in % | Levels of impurity of Formula II in % | Increase in total impurities from initial |
| Comparative Example 2 | pH 3.4 | 2.40 | 0.48 | 3.10 |
| | pH 3.7 | 1.15 | 0.59 | 2.09 |
| | pH 3.8 | 1.47 | 0.75 | 2.67 |
| | pH 3.9 | 0.89 | 0.74 | 2.04 |
| Example 3 (an embodiment of the disclosed dosage form) | pH 4.1 | 0.62 | 0.50 | 1.42 |
| | pH 4.5 | 0.29 | 0.39 | 0.90 |
| | pH 4.8 | 0.33 | 0.33 | 0.82 |

The parenteral unit dosage form comprising aqueous solution of dihydroergotamine or its pharmaceutically acceptable salt having a pH of 4.2 to 4.8 (±0.1), when placed in an overwrap pouch without an oxygen scavenger and stored at 25° C. and 60% relative humidity or at 40° C. and 75% relative humidity, showed substantially lower amount of impurity of Formula I and lower amount of total impurities compared to a parenteral unit dosage forms that comprise aqueous solution of dihydroergotamine having a lower pH of 3.4 to 3.9. Particularly, the % of impurity of formula I present in solution with pH 4.5 to 4.8 is significantly lower compared to that present in solution with pH 3.4 to 3.8. It was further observed that there was not much impact of pH on the content of impurity of formula II, although the observed values for solution having pH of 4.5 to 4.8 were lower compared to solution having pH 3.4 to 3.8.

When the pH of the aqueous solution was less than 3.5, very high levels of known and unknown impurities were generated upon storage. For example, when the pH of the aqueous solution was adjusted to 3.4, 0.76% by weight of an impurity of Formula I and 1.42% by weight of an impurity of Formula II were generated and the increase in total amount of impurities as compared to an initial amount was 3.11%, when the solution contained in the dosage form was stored at 25° C. and 60% relative humidity for three months. Also, 2.40% by weight of an impurity of Formula I, 0.48% by weight of an impurity of Formula II and 3.10% increase in total amount of impurities as compared to an initial amount were generated when stored at 40° C. and 75% relative humidity just for one month.

On the contrary, for parenteral unit dosage form comprising aqueous solution of dihydroergotamine having a pH of 4.5, only 0.12% by weight of an impurity of Formula I and 0.97% by weight of an impurity of Formula II were generated and the increase in total amount of impurities as compared to an initial amount were also lower at 1.59%, when the dosage form was stored at 25° C. and 60% relative humidity for three months. Also, even upon storage at 40° C. and 75% relative humidity for one month, merely 0.29% by weight of an impurity of Formula I, 0.39% by weight of an impurity of Formula II and 0.9% increase in total amount of impurities as compared to the initial amount of impurities was observed.

Example 4

An available commercial product is, D.H.E. 45® Injection manufactured by Valeant Pharmaceuticals. D.H.E. 45® Injection is a glass ampoule with an aqueous solution containing 1 mg/ml of dihydroergotamine mesylate, ethanol 6.1% by weight, glycerol 15% by weight, pH adjusting agent and water for injection. The ampoules are packaged in carton. Three marketed samples of this product from different manufacturing lots were procured and stored at room temperature. The ampoules were packaged in carton during storage. The samples were tested for pH and impurity levels, namely impurity of Formula I and impurity of Formula II, at the near expiry period. The results of the chemical stability are tabulated in Table No. 12. Also, the chemical stability of the Example 2 of the present invention (pH of 4.2) having aqueous solution of dihydroergotamine filled in a pre-filled syringe and overwrapped in an aluminium pouch with oxygen scavenger was tested at 40° C. and 75% relative humidity and the results are tabulated in Table 12.

TABLE 12

Chemical stability of Marketed product (Example 4) versus Example 2

| Samples Tested | | Batch/lot Number | When stored at room temperature (time point -near expiry date of the product) | |
|---|---|---|---|---|
| | | | Levels of impurity of Formula I in % | Levels of impurity of Formula II in % |
| Samples of Marketed Product D.H.E 45 ® Injection by Valeant Pharmaceuticals | pH 3.85 pH 3.75 pH 4.01 | 4B141A 4N417A 4K147A | 4.30 4.39 3.14 | 0.40 0.54 0.73 |
| Example 2 (an embodiment of the disclosed formulation) | — | | Levels of impurity of Formula I in % | Levels of impurity of Formula II in % |
| Aqueous solution of Table 9 having pH 4.2 | | | When stored for three Months at 40° C. and 75% relative humidity | |
| | | | 1.55 | 0.11 |
| | | | When stored for six months at 40° C. and 75% relative humidity that corresponds to 2 years at room temperature storage | |
| | | | 2.98 | 0.13 |

The pH of the aqueous solution of the commercial product was about 3.8. The levels of impurity of Formula I as well as Formula II were found to be significantly higher compared to that observed for Example 2 (an embodiment of the disclosed dosage form), despite the fact that the marketed product was contained in an ampoule which is a sealed container with no rubber contact parts and was kept in a carton. In contrast, in case of Example 2 (an embodiment of the disclosed dosage form), the solution is contained in the reservoir of pre-filled syringe which is sealed by an elastomeric stopper, and the solution remains in direct contact with the elastomeric stopper during storage; yet the levels of impurity of Formula I and Formula II were minimal. Surprisingly, the impurity of Formula II was just 0.13% when stored for six months at 40° C. and 75% relative humidity, which corresponds to more than two-year shelf life when stored at room temperature. Thus, the disclosed dosage form provides an improved parenteral unit dosage form which is not only user friendly but is stable and robust with respect to storage condition of the parenteral unit dosage form.

We claim:

1. A method for effecting acute treatment of migraine or cluster headache episodes, comprising administering dihydroergotamine or a pharmaceutically acceptable salt thereof to a subject in need thereof, wherein said administering comprises injecting said dihydroergotamine or pharmaceutically acceptable salt thereof from an auto-injector or pre-filled syringe of a parenteral unit dosage form comprising an aqueous solution of dihydroergotamine or a pharmaceutically acceptable salt thereof as a sole active ingredient, and one or more pH adjusting agents, wherein:
   the pH of the aqueous solution is in the range of 4.1 to 4.9,
   the solution is contained in the auto-injector or the pre-filled syringe, and
   the solution does not require reconstitution or dilution prior to administration.

2. The method according to claim 1, wherein said injecting is by subcutaneous injection.

3. The method according to claim 1, wherein said injecting is by intramuscular injection.

4. The method according to claim 1, wherein the pH of the aqueous solution is in the range of 4.2 to 4.8.

5. The method according to claim 1, wherein the aqueous solution is free of one or both of preservative agents and complexing agents.

6. The method according to claim 1, wherein the pharmaceutically acceptable salt of dihydroergotamine is dihydroergotamine mesylate and it is present at a concentration of from 0.5 mg/ml to 1.5 mg/ml.

7. The method according to claim 1, wherein the aqueous solution further comprises one or more co-solvents.

8. The method according to claim 1, wherein the aqueous solution comprises dihydroergotamine or a pharmaceutically acceptable salt thereof at a concentration of from 0.75 to 1.5 mg/ml, ethanol, glycerine, methane sulfonic acid, sodium hydroxide, and water.

9. The method according to claim 1, wherein the aqueous solution comprises dihydroergotamine mesylate at a concentration of 1 mg/ml, ethanol, glycerine, methane sulfonic acid, sodium hydroxide, and water.

* * * * *